(12) United States Patent
Hirosawa

(10) Patent No.: US 7,034,940 B1
(45) Date of Patent: Apr. 25, 2006

(54) METHOD FOR EVALUATING DISPLAYING ELEMENT OF LIQUID CRYSTAL, INFORMATION STORAGE MEDIUM FOR STORING COMPUTER PROGRAM REPRESENTATIVE OF THE METHOD AND EVALUATING SYSTEM USING THE SAME

(75) Inventor: Ichiro Hirosawa, Tokyo (JP)

(73) Assignee: NEC Electronics Corporation, Kanagawa (JP)

( * ) Notice: Subject to any disclaimer, the term of this patent is extended or adjusted under 35 U.S.C. 154(b) by 954 days.

(21) Appl. No.: 09/722,281

(22) Filed: Nov. 28, 2000

(30) Foreign Application Priority Data

Dec. 3, 1999   (JP) .......................................... 11-345107

(51) Int. Cl.
*G01J 4/00*   (2006.01)

(52) U.S. Cl. ........................................ 356/369; 356/364
(58) Field of Classification Search ................. 356/364, 356/365, 369
See application file for complete search history.

(56) References Cited

U.S. PATENT DOCUMENTS 5,532,823 A * 7/1996 Fukui et al. ................. 356/364
5,966,195 A * 10/1999 Sato et al. .................. 349/187
6,081,337 A * 6/2000 Kwok et al. ................ 356/601
6,157,448 A * 12/2000 Kowa et al. ................ 356/365

FOREIGN PATENT DOCUMENTS

| JP | 4-307312 | 10/1992 |
|---|---|---|
| JP | A 6-265840 | 9/1994 |
| JP | 8-184413 | 7/1996 |
| JP | A 9-89760 | 4/1997 |
| JP | A 9-218133 | 8/1997 |
| JP | A 9-243510 | 9/1997 |
| JP | A 11-84335 | 3/1999 |
| JP | A 11-160198 | 6/1999 |
| JP | A 11-258110 | 9/1999 |
| JP | A 11-304645 | 11/1999 |
| KR | B1 10-0158045 | 8/1998 |

* cited by examiner

*Primary Examiner*—Zandra V. Smith
(74) *Attorney, Agent, or Firm*—Young & Thompson

(57) ABSTRACT

An evaluating apparatus uniquely determines a twist angle, a cell gap and a mean tilt angle through a method, in which a linearly polarized light beam is firstly radiated to a sample of liquid crystal display element so as to produce a transmitted light beam, subsequently, a photo-multiplier measures at least one of a directional dependency of a polarization of the transmitted light beam and a wavelength dependency of the polarization of the transmitted light beam and, finally, a computer system determines the twist angle, the mean tilt angle the cell gap on the basis of the directional dependency or the wavelength dependency.

19 Claims, 16 Drawing Sheets

DIRECTION OF SAMPLE (deg)

~ 5.00 μm 5.00 ~ 5.10 μm 5.10 ~ 5.20 μm 5.20 ~ 5.30 μm 5.30 μm ~

| | |
|---|---|
| ☐ | ~ 5.00 μm |
| ▦ | 5.00 ~ 5.10 μm |
| ▨ | 5.10 ~ 5.20 μm |
| ▩ | 5.20 ~ 5.30 μm |
| ■ | 5.30 μm ~ |

| | |
|---|---|
| ☐ | ~88.0° |
| ▦ | 88.0~88.5° |
| ▨ | 88.5~90.0° |
| ▩ | 90.0~90.5° |
| ■ | 90.5°~ |

METHOD FOR EVALUATING DISPLAYING ELEMENT OF LIQUID CRYSTAL, INFORMATION STORAGE MEDIUM FOR STORING COMPUTER PROGRAM REPRESENTATIVE OF THE METHOD AND EVALUATING SYSTEM USING THE SAME

FIELD OF THE INVENTION

This invention relates to a method for evaluating liquid crystal display elements and an evaluating system used therein and, more particularly, to a method for measuring a twisting angle and a mean tilt angle of liquid crystal and the thickness of liquid crystal layer, an apparatus used therein and a method for evaluating a regulatory ability of a substrate for orientation of liquid crystal.

DESCRIPTION OF THE RELATED ART

A method for measuring the thickness of liquid crystal layer is disclosed in Japanese Patent Publication of Unexamined Application No. 4-307312. The thickness of liquid crystal layer is equal to the gap between the substrates, and, accordingly, is referred to as "cell gap". According to the Japanese Patent Publication of Unexamined Application, when a continuous polarized light beam is incident onto a liquid crystal element, the intensity of transmitted light exhibits wavelength dependency, i.e., the dependence on the wavelength. Using the wavelength dependency, the Japanese Patent Publication of Unexamined Application proposes to determine the cell gap on the basis of the intensity of the transmitted light.

Another prior art measuring system determines the cell gap on the basis of the intensity of reflection. A convergent light beam is assumed to have an extremely small depth of focus in a confocal system. When the convergent light beam is incident onto a sample, the intensity of reflection exhibits focal position dependency, i.e., dependence on the focal position. Using the focal position dependency, the cell gap is determined.

As to the twist angle, Japanese Patent Publication of Unexamined Application Nos. 6-265839 and 6-265840 propose to determine the degree of anchoring on the basis of the intensity of transmitted light passing through liquid crystal filling the gap between a polarizer and an analyzer.

As to the cell gap and the twist angle, Japanese Patent Publication of Unexamined Application No. 8-184413 proposes to determine the cell gap and the twist angle on the basis of the direction of two pairs of liquid crystal displaying elements and the direction of a polarizer/analyzer. The prior art system includes a monochromatic light source, the polarizer, the two pairs of liquid crystal displaying elements, the analyzer and a photo-detector. The monochromatic light is radiated from the monochromatic light source, and passes through the polarizer, the two pairs of liquid crystal displaying elements and the analyzer. The monochromatic light is incident onto the photo-detector. The photo-detector measures the intensity of the incident light. The direction of polarizer/analyzer and the direction of two pairs of liquid crystal displaying elements are changed. The intensity of incident light is plotted, and the local minimum value is determined. The direction of polarizer/analyzer and the direction of two pairs of liquid crystal displaying elements are read at the local minimum value, and the cell gap and the twist angle are determined on the basis of the direction of polarizer/analyzer and the direction of two pairs of liquid crystal displaying elements.

Japanese Patent No. 2778935 proposes to measure the cell gap and the twist angle for determining the degree of anchoring. The cell gap and the twist angle are determined on the basis of the direction of an analyzer and the direction of liquid crystal elements at the local minimum value of the intensity of transmitted light. In order to enhance the accuracy, the prior art measuring system includes a light source, a polarizer, the liquid crystal displaying elements, the analyzer, a photo-detector and a photo-elastic element.

The cell gap is determined by utilizing the difference in refractive index between the liquid crystal and the substrate in the prior art method utilizing the wavelength dependency and the prior art method utilizing the cofocal system. However, the twist angle, which features the structure of the liquid crystal displaying elements, is not determined through the prior art methods. Although the prior art methods disclosed in Japanese Patent Publication of Unexamined Application Nos. 6-265839 and 6-265840 are able to be used for determining the twist angle, it is necessary that the cell gap has been already known.

The prior art methods disclosed in Japanese Patent Publication of Unexamined Application No. 8-184413 and Japanese Patent No. 2778935 are used for determining the cell gap and the twist angle on the basis of the direction of two pairs of liquid crystal displaying elements and the direction of the polarizer/analyzer at the local minimum value of the intensity of the transmitted light as described hereinbefore. However, the prior art methods merely teach the combination of the cell gap and the twist angle. There are plural combinations which give the direction of liquid crystal displaying elements and the direction of polarizer/analyzer. In order to determine the cell gap of a given sample or the twist angle of the given sample, it is necessary to have known the twist angle or the cell gap.

The accuracy of the combination of the cell gap and the twist angle is dependent on the precision of the measurement, i.e., the measuring the direction of the liquid crystal displaying elements and the direction of the analyzer. However, it is not easy to precisely measure the direction of the liquid crystal displaying elements and the direction of the analyzer. In case where the combination of the cell gap and the twist angle is close to the Morgan limit, the transmitted light varies the intensity a little, and it is hard to determine the local minimum intensity. This means that the direction of the liquid crystal displaying elements and the direction of the polarizer/analyzer are less accurate. If the combination of the cell gap and the twist angle satisfies the Morgan limit, the intensity of the transmitted light is not dependent on the direction of the sample, and the cell gap and the twist angle are not determined.

SUMMARY OF THE INVENTION

It is therefore an important object of the present invention to provide an evaluating method, which is free from the problems inherent in the prior art methods.

It is also an important object of the present invention to provide an information storage medium, which stores a computer program representative of the method according to the present invention.

It is also an important object of the present invention to provide an evaluating system in which the evaluating method is realized.

In accordance with one aspect of the present invention, there is provided a method for evaluating a liquid crystal display element comprising the steps of a) radiating a light beam having a certain waveband and a predetermined polarization to the liquid crystal display element so as to produce a transmitted light beam, b) measuring at least one of a directional dependency of a polarization of the transmitted light beam and a wavelength dependency of the polarization of the transmitted light beam, and c) determining at least one of a twist angle, of the liquid crystal confined in the liquid crystal display element, a mean tilt angle of the liquid crystal and a thickness of the liquid crystal on the basis of the at least one of the directional dependency and the wavelength dependency.

In accordance with another aspect of the present invention, there is provided a method for evaluating a liquid crystal display element comprising the steps of a) radiating a light beam having a certain waveband and a predetermined polarization to a portion of the liquid crystal display element so as to produce a transmitted light beam, b) measuring at least one of a directional dependency of a polarization of the transmitted light beam and a wavelength dependency of the polarization of the transmitted light beam, c) moving the liquid crystal display element on a virtual plane perpendicular to the optical axis of the light beam so that the light beam is incident onto another portion of the liquid crystal display element, d) repeating the step b) for the another portion of the liquid crystal display element, and e) determining a dispersion of at least one of a twist angle, of the liquid crystal confined in the liquid crystal display element, a mean tilt angle of the liquid crystal and a thickness of the liquid crystal on the basis of the at least one of the directional dependency and the wavelength dependency.

In accordance with yet another aspect of the present invention, there is provided an information storage medium for storing a computer program representative of a method for evaluating a liquid crystal display element, and the method comprises the steps of a) radiating a light beam having a certain waveband and a predetermined polarization to the liquid crystal display element so as to produce a transmitted light beam, b) measuring at least one of a directional dependency of a polarization of the transmitted light beam and a wavelength dependency of the polarization of the transmitted light beam, and c) determining at least one of a twist angle, of the liquid crystal confined in the liquid crystal display element, a mean tilt angle of the liquid crystal and a thickness of the liquid crystal on the basis of the at least one of the directional dependency and the wavelength dependency.

In accordance with still another aspect of the present invention, there is provided an information storage medium for storing a computer program representative of a method for evaluating a liquid crystal display element, and the method comprises the steps of a) radiating a light beam having a certain waveband and a predetermined polarization to a portion of the liquid crystal display element so as to produce a transmitted light beam, b) measuring at least one of a directional dependency of a polarization of the transmitted light beam and a wavelength dependency of the polarization of the transmitted light beam, c) moving the liquid crystal display element on a virtual plane perpendicular to the optical axis of the light beam so that the light beam is incident onto another portion of the liquid crystal display element, d) repeating the step b) for the another portion of the liquid crystal display element, and e) determining a dispersion of at least one of a twist angle, of the liquid crystal confined in the liquid crystal display element, a mean tilt angle of the liquid crystal and a thickness of the liquid crystal on the basis of the at least one of the directional dependency and the wavelength dependency.

In accordance with yet another aspect of the present invention, there is provided an evaluating apparatus for a liquid crystal display element, comprising a light source radiating a light beam toward the liquid crystal display element, a polarizer provided between the light source and the liquid crystal display element for producing a polarized light beam from the light beam, a sample stage keeping the liquid crystal display element on an optical axis of the polarized light beam, an analyzer provided on the optical axis of the polarized light beam, a light intensity measuring unit for measuring a light intensity of a transmitted light beam passing through the analyzer and producing data information representative of the light intensity, and a data processing system selectively connected to the light source, the polarizer, the sample stage and the analyzer for controlling the attitude thereof and to the light intensity measuring unit for receiving the data information and measuring at least one of a directional dependency of a polarization of the transmitted light beam and a wavelength dependency of the polarization of the transmitted light beam so as to determine at least one of a twist angle, of the liquid crystal confined in the liquid crystal display element, a mean tilt angle of the liquid crystal and a thickness of the liquid crystal.

BRIEF DESCRIPTION OF THE DRAWINGS

The features and advantages of the evaluating method and the evaluating system will be more clearly understood from the following description taken in conjunction with the accompanying drawings in which.

DESCRIPTION OF THE PREFERRED EMBODIMENTS

Figure 1:
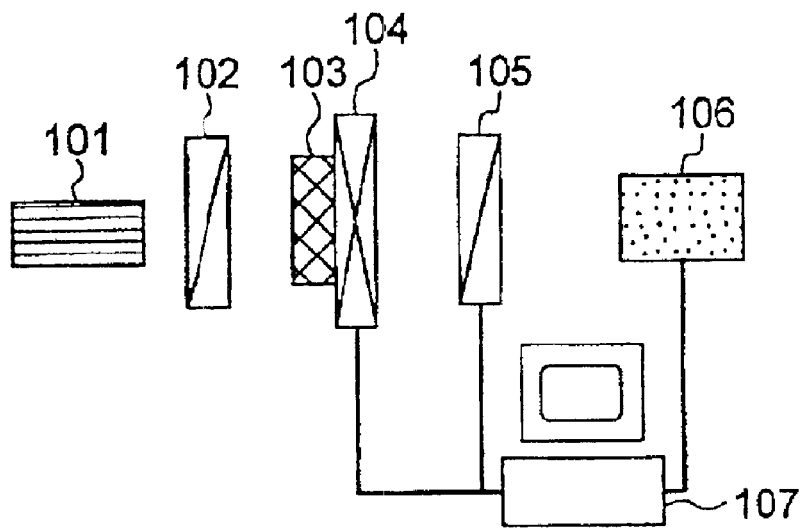
FIG. 1 is a schematic view showing an evaluating system according to the present invention.

The polarization of light is described by the ratio of Ep/Es and the phase difference $\Delta$. Ep represents the amplitude of an electric field component parallel to one of the two axes defining a normal rectangular coordinate system on a plane vertical to the progressive light, and Es represents the amplitude of another electric field component vertical to the electric field component. The electric field components have the phase difference $\Delta$. When tangent $\psi$ is equal to Ep/Es, the angle $\psi$ stands for the ratio Ep/Es. In general, the electric field components Es and Ep are moved on an elliptical orbit in the normal rectangular coordinate system on the plane vertical to the progressive light.

In the prior art methods for determining the cell gap and the twist angle, determining the direction of analyzer at the local minimum intensity of transmitted light is equivalent to determining the direction of the minor axis of the ellipse. Therefore, the polarization of the transmitted is imperfectly determined by the direction of the analyzer. The liquid crystal display element controls the polarization of transmitted light, and the properties of the liquid crystal display element are to be determined through determining the polarization of the transmitted light. In order to determining the polarization of transmitted light, polarized monochromatic light is incident on the image producing surface of a liquid crystal display element, and the polarization of the transmitted light is determined. Even if the cell gap and the twist angle of a sample are close to the Morgan limit, the cell gap and the twist angle are accurately determined on the basis of the relation between the polarization of the incident light and the polarization of the transmitted light or the relation between the direction of the sample and the polarization of the transmitted light. Moreover, the polarization of transmitted light is further dependent on the mean tilt angle of liquid crystal molecules. The polarization of transmitted light has the dependence on the direction of a sample, and the dependence is hereinbelow referred to as "direction dependency". If the direction dependency is accurately measured, it is possible to determine the mean tilt angle.

Although the direction dependency is determined, it is necessary that either cell gap or twist angle range has been known, because there are a plurality of combinations between the cell gap and the twist angle. The direction dependency is non-linearly varied together with the wavelength of the incident light. The present invention proposes to radiate plural light components to a surface of a liquid crystal display element for determining the direction dependency. The light components are different in wavelength from and identical in polarization with one another. The polarization of each transmitted light component has dependence on the polarization of the corresponding incident light component. The dependence between the polarization of each transmitted light component and the polarization of the associated incident light component is hereinbelow referred to as "polarization dependency". Moreover, the polarization of each transmitted light component has the dependence on the direction of the sample. Using the polarization dependency or the direction dependency, the cell gap and the twist angle are uniquely determined. If the direction dependency is accurately measured, the mean tilt angle is further determined.

A white light source is used as the incident light source, and is combined with a spectroscope for measuring the wavelength dispersion of the direction dependency. Then, the cell gap and the twist angle are uniquely determined as similar to the method using plural light components different in wavelength.

In case where the sample's direction is constant, periodicity, which is dependent on the cell gap is observed in the wavelength dispersion of the polarization of the transmitted light under the condition that the wavelength intervals is equal to 50 nanometers or less. The cell gap and the twist angle are uniquely determined through the observation of the direction dependency for one or more than one incident light component. If the wavelength dispersion of the polarization of the transmitted light and the direction dependency are accurately measured, it is possible to determine the mean tilt angle of liquid crystal molecules.

If a suitable mechanisms gives rise to movement of a sample on a plane, dispersion of the cell gap and the twist angle or dispersion of the cell gap, the twist angle and the mean tilt angle of liquid crystal molecules are determined in the plane.

First Embodiment

FIG. 1 shows an evaluating system embodying the present invention. Reference numeral 101 designates a light source. The light source 101 is implemented by a He-Ne laser emitting device, and radiates a light beam through a polarizer 102 to a sample to be evaluated. In other words, the optical axis rightward extends from the light source 101 in FIG. 1. The sample 103 is attached to a sample stage 104, and rotates the sample 103 around the optical axis. The sample stage 104 is equipped with an encoder, and the direction of the sample 103 is read by using the encoder. An analyzer 105 is associated with the sample stage 104, and is rotatable around the optical axis. The analyzer 105 is equipped with an encoder, and the direction of the analyzer 105 is read by using the encoder. The light beam passes the polarizer 102, the sample 103 and the analyzer 105, and is fallen onto a photo-detector 106. The photo-detector 106 determines the intensity of the incident light. In this instance, the photo-detector 106 is implemented by a photo-multiplier. The sample stage 104, the analyzer 105 and the photo-detector 106 are connected to a computer system 107. The computer system 107 controls the direction of the sample stage 104 and the direction of the analyzer 105. The polarization of the transmitted light has dependence on the direction of the sample 103, i.e., the direction dependency. The computer system 107 calculates the direction dependency of the transmitted light on the basis of the intensity of the transmitted light detected by the photo-detector 106, and determines the cell gap of the sample 103, the twist angle and the mean tilt angle.

Two orthogonal directions are assumed. The two orthogonal directions are on a plane vertical to the progressive light. The electric field vector of the light is assumed to have s-component which is parallel to one of the two orthogonal directions and p-component which is in parallel to the other of the two orthogonal directions. The polarizer 102 is oriented in such a manner as to produce linearly polarized light in which the ratio between the s-component and the p-component is 1:1. The polarizer 102 is inclined at 45 degrees with respect to both of the s-component and the p-component. The polarization of the transmitted light is determined through a method of rotational analyzer. The polarization of light passing through the sample is determined on the basis of the detected light intensity dependent on the direction of the analyzer through the method of rotational analyzer. The detected light intensity is measured at intervals of 2 degrees, i.e., 180 directions.

Sample A was fabricated as follows. Two glass plates were prepared. The glass plate measured 30 millimeters wide, 40 millimeters long and 1.1 millimeters thick. Polyimide was spun onto the glass plates. The polyimide was manufactured by Nissan Chemical Corporation, and was sold as PI-A. The polyimide was dried in an oven at 80 degrees in centigrade for 15 minutes. Thereafter, the oven was raised to 250 degrees in centigrade, and the polyimide was sintered for 60 minutes. A rubbing roller was prepared. Rayon fibers were implanted into the rubbing roller, and the diameter of the rubbing roller was 3 centimeters. The rubbing roller was driven for rotation at 800 rpm. The pushing length was 0.3 millimeter, and the rubbing roller was moved at 20 millimeters per second. The rubbing was repeated three times at room temperature. The glass plates were arranged in such a manner that the rubbing direction on one glass plate crossed the rubbing direction on the other glass plate at 90 degrees. The diameter of spacers was 5 millimeters, and the spacers were mixed in two-liquid adhesive compound in epoxy system. Using the two-liquid adhesive compound, the glass plates were assembled together. Liquid crystal was injected into the space between the glass plates through the capillary phenomenon. The liquid crystal exhibited the transition temperature of 62 degrees in centigrade and the refractive index of 1.586 and 1.510 for 633-wavelength light. The injection port was sealed with adhesive compound in epoxy system. Thereafter, the resultant cell structure was treated with heat in an oven at 90 degrees in centigrade for 2 hours. Thus, the liquid crystal orientation was uniformed through the isotropic process.

Figure 2:
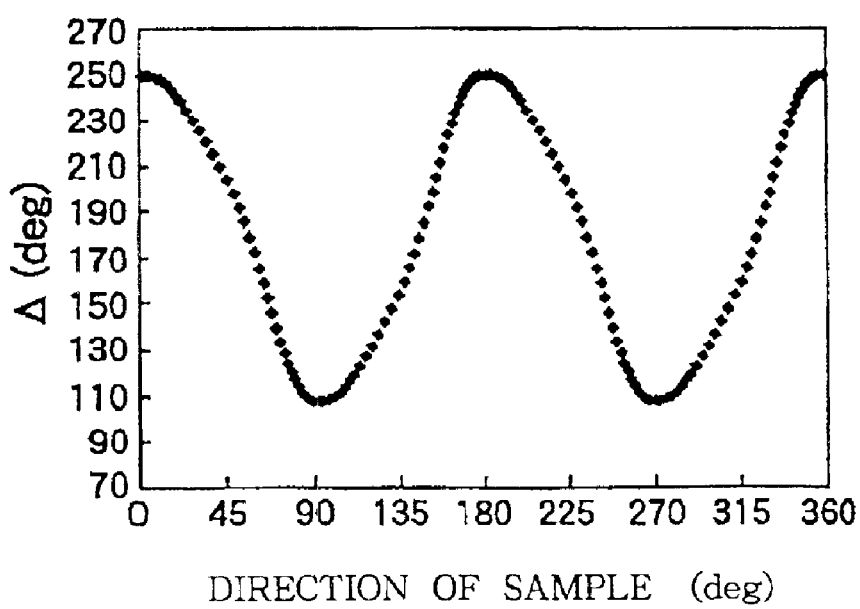
FIG. 2 is a graph showing relation between the phase difference of transmitted light and the direction of a sample.
Figure 3:
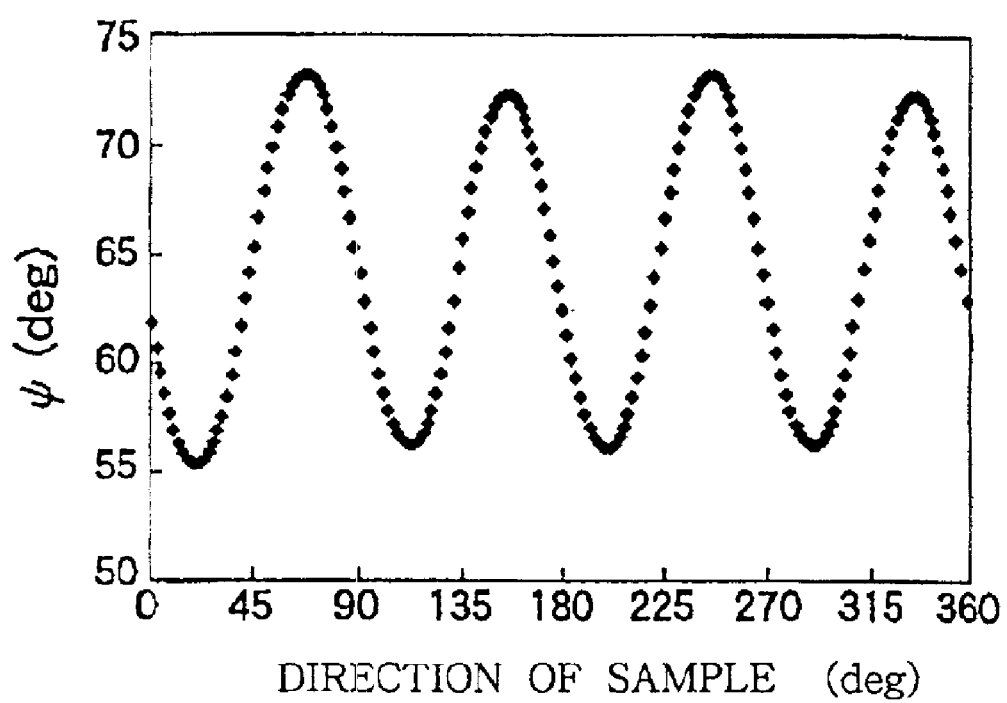
FIG. 3 is a graph showing relation between the amplitude ratio of the transmitted light and the direction of the sample.

Sample A was attached to the sample stage 104, and the light was radiated from the light source 101 to sample A. The transmitted light passed through the analyzer 105, and was incident onto the photo-detector 106. The polarization was expressed by the amplitude ratio $E_p/E_s$ and the phase difference $\Delta$, and the angle $\psi$ stood for the amplitude ratio $E_p/E_s$ as described hereinbefore. The phase difference $\Delta$ and the angle $\psi$ of the transmitted light were plotted with respect to the direction of sample A in FIGS. 2 and 3. The rotational symmetry was observed in FIGS. 2 and 3. The cell gap and the twist angle of sample A were determined on the basis of the experimental result as follows.

Light with wavelength $\lambda$ is assumed to a liquid crystal element. Liquid crystal has the refractive index Ne and No. The cell gap is d, the twist angle is $\phi$, the mean tilt angle is $\theta$ and the direction is zero with respect to the s-component. 2.2 Jones matrix exhibits the optical properties of the liquid crystal element, and elements J11, J12, J21 and J22 of the Jones matrix are expressed as $J11 = \sin(\phi)\sin(\phi V) + \cos(\phi)\cos(\phi V)/V + iU\cos(\phi)\sin(\phi V)/V$ $J12 = \cos(\phi)\sin(\phi V) - \sin(\phi)\cos(\phi V)/V - iU\sin(\phi)\sin(\phi V)/V$ $J21 = \cos(\phi)\sin(\phi V) + \sin(\phi)\cos(\phi V)/V + iU\sin(\phi)\sin(\phi V)/V$ $J22 = \sin(\phi)\sin(\phi V) + \cos(\phi)\cos(\phi)/V - iU\cos(\phi)\sin(\phi)/V$ where i is the imaginary unit and U and V are expressed as $U = \pi d (Ne\{1 + (Ne^2/No^2 - 1)\sin^2\theta\}^{-1/2} - No)/\lambda\phi$ $V = (1 + U^2)^{1/2}$ If the direction of the liquid crystal element is inclined at A with respect to the s-component of the light, the elements J11(A), J12(A), J21(A) and J22(A) of Jones matrix are $J11(A) = J11 \cos^2(A) - (J12 + J21)\sin(A)\cos(A) + J22 \sin^2(A)$ $J12(A) = J12 \cos^2(A) + (J11 - J22)\sin(A)\cos(A) - J21 \sin^2(A)$ $J21(A) = J21 \cos^2(A) + (J11 - J22)\sin(A)\cos(A) - J12 \sin^2(A)$ $J22(A) = J22 \cos^2(A) + (J12 + J21)\sin(A)\cos(A) + J11 \sin^2(A)$ As described hereinbefore, the incident light is linearly polarized, and the ratio between s-component and p-component is 1:1. The s-component of the transmitted light is J11(A)+J12(A). The p-component is expressed by angle $\psi$, the tangent of which, i.e., $\tan \psi(A)$ gives the phase difference $\Delta(A)$ of J21(A)+J22(A) from the s-component J11(A)+J12(A) and the ratio of the absolute values thereof |J21(A)+J22(A)|/|J11(A)+J12(A)|. The differences between the calculated polarization $\Delta(A)/\psi(A)$ and the measured polarization $\Delta/\psi$ are squared, and the square numbers are added together. The twist angle $\phi$ and the cell gap d are determined at the local minimum of the sum.

The solution for the polarization $\Delta(A)/\psi(A)$ is hardly obtained through the standard methods of least squares such as Marcut method, brachistochrone method and Gauss-Newton method. In order to obtain the solution, the cell gap d and the twist angle $\phi$ are varied in a certain range at predetermined intervals. The differences are calculated between the measured values and the calculated values of $\Delta(A)$ and $\psi(A)$. The differences are squared, and the sum of the square numbers is determined. In detail, the twist angle is varied from $\phi$min and $\phi$max at intervals of $\delta$. The conditions are ($\phi$max−$\phi$min)/$\delta$+1. On the other hand, the cell gap is varied from dmin to dmax at intervals of $\eta$ for each twist angle. The conditions are (dmax−dmin)/$\eta$+1. The conditions are ($\phi$max−min)/$\delta$+1. The polarization $\Delta(A)/\psi(A)$ is calculated for each of the combinations between {($\phi$max−$\phi$min)/$\delta$+1} and {(dmax−dmin)/$\eta$+1}. Thus, a set of values each representative of the sum of squares is obtained.

The set is searched for the cell gap d1 and the twist angle $\psi$1 which give the least value of the sub of squares. If the precision to be required is greater than the cell gap and the twist angle to be calculated. The cell gap range from (d1−$\eta$) to (d1+$\eta$) is divided by a value less than $\eta$ such as, for example, $\eta$/10 for calculating the polarization. As to the twist angle, the twist angle range from ($\phi$1−$\delta$) to ($\phi$1+$\delta$) is divided by a value less than $\delta$ such as, for example, $\delta$/10. The total combinations are 121. The polarization is calculated for each of the 121 combinations. The differences between the measured values and the calculation results are squared, and the squares are summed. Another set of values each representative of the sum of squares is obtained. The set is searched for the cell gap d2 and the twist angle $\phi$ which gives the least value of the sum of squares. The above-described sequence is repeated until the cell gap intervals and the twist angle intervals become less than the precision to be required.

In case where the rubbing direction is unknown, the polarization $\Delta(A)/\psi(A)$ is firstly calculated as described hereinbefore. The direction Amax which gives the maximum value of each $\Delta(A)$ or $\psi(A)$ and the direction Amin which gives the minimum value of each $\Delta(A)$ or $\psi(A)$ are compared with the direction Omax which gives the maximum value of the polarization $\Delta/\psi$ and the direction Omin which gives the minimum value of the polarization $\Delta/\psi$, and the rubbing direction is estimated through the comparison. The direction dependency of the polarization is assumed to be $\Delta(A-Amax+Omax)/\psi(A-Amax+Omax)$ or $\Delta(A-Amin+Omin)/\psi(A-Amin+Omin)$, and the polarization is recalculated. The differences are calculated between the measured values and the calculated values, and the sum of squares is determined.

Figure 4:
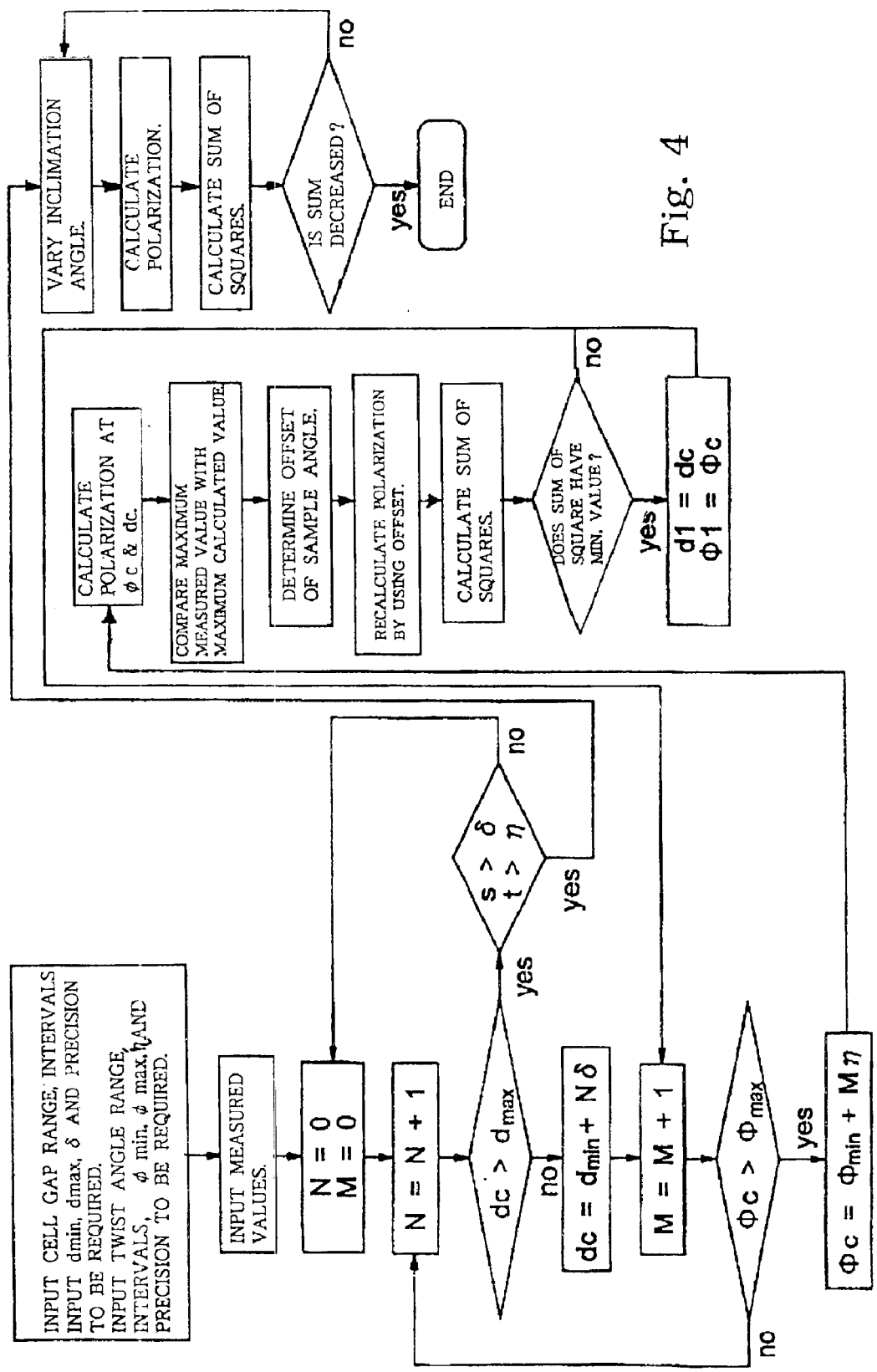
FIG. 4 is a flowchart showing a method for evaluating a liquid crystal display element according to the present invention.

A computer program represents the above-described method as shown in FIG. 4, and is stored in the computer system 107. In case of sample A, the twist angle and the cell gap were estimated to be of the order of 90 degrees and of the order of 5 microns. The twist angle range was from 80 degrees to 100 degrees, and the cell gap range was from 4 microns to 6 microns. The mean tilt angle of the liquid crystal was varied from zero to 5 degrees at intervals of 1 degrees. The polarization was measured by using the measuring apparatus shown in FIG. 1 and calculated as described hereinbefore. The sum of squares was calculated. When the mean tilt angle was 3 degrees, the sum of squares was minimized.

When the mean tilt angle of the liquid crystal is adjusted to zero, the cell gap, the twist angle and the mean tilt angle were estimated to be 5.13 microns, 89.8 degrees and 3 degrees through the computer program shown in FIG. 4.

Figure 5:
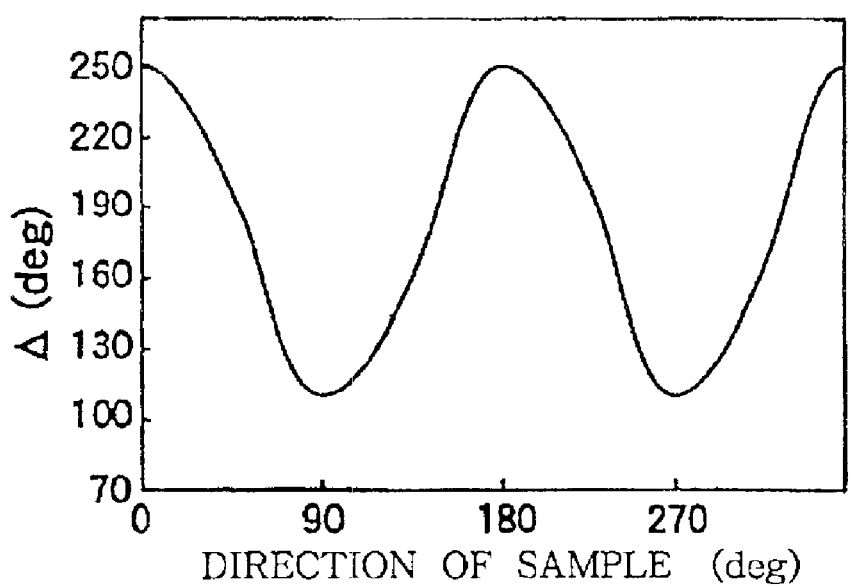
FIG. 5 is a graph showing dependence of a phase difference on the direction of a sample plotted through calculations.
Figure 6:
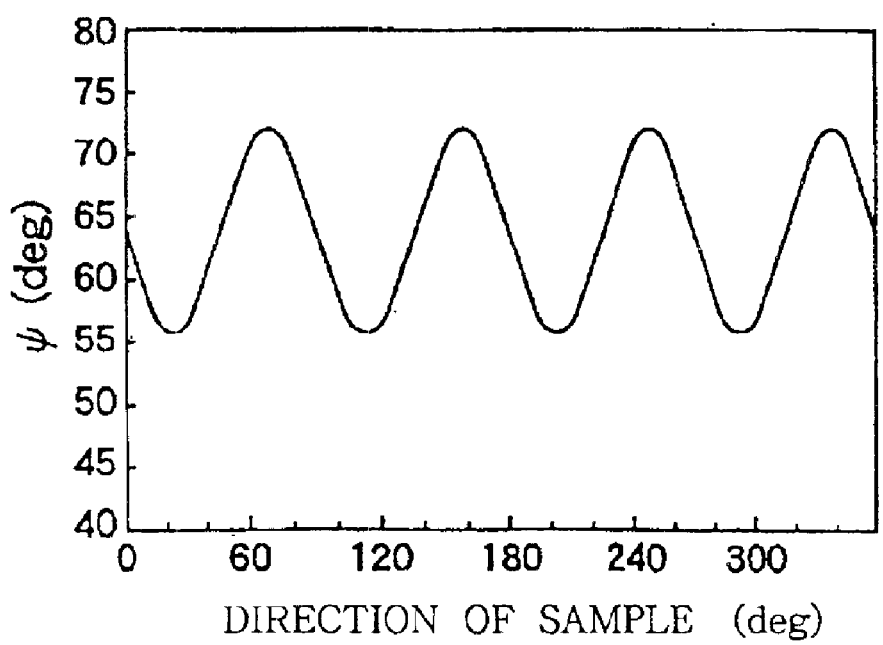
FIG. 6 is a graph showing dependence of an amplitude ratio on the direction of the sample plotted through calculations.

The direction dependency of the phase difference $\Delta$ is shown in FIG. 5, and the direction dependency of the amplitude ratio $\psi$ is shown in FIG. 6. The phase difference $\Delta$ and the amplitude ratio $\psi$ were calculated. The rotational analyzing method was employed. In the rotational analyzing method, the analyzer 105 was rotated for modulating the light incident on the analyzer 105, and the polarization is determined. A rotational phase plate method may be used. In the rotational phase plate method, a phase plate such as, for example, a quarter wavelength plate is inserted so as to modulate it to the light intensity by rotating the phase plate. The polarization may be determined through another employable method using a photo-elastic element to be electrically modulated.

Second Embodiment

The evaluating system shown in FIG. 1 was used for sample B for measuring the polarization of transmitted light. Sample B was fabricated as follows. Glass plates were prepared. The glass plate measured 30 millimeters wide, 40 millimeters long and 1.1 millimeters thick. Polyimide PI-B manufactured by Nissan Chemical Corporation was spun onto the glass plates. The polyimide was dried in an oven at 80 degrees in centigrade for 15 minutes. Thereafter, the polyimide was sintered in the oven at 180 degrees in centigrade for 60 minutes. Using a rubbing roller implanted with rayon fibers, the polyimide layers were rubbed three times at room temperature. The diameter of the rubbing roller was 3 centimeters, and was driven for rotation at 800 rpm. The push length was 0.3 millimeter, and the rubbing roller was moved at 20 millimeters per second. The rubbing direction on each glass plate was adjusted to 50 degrees, and the glass plates were assembled together by using two-liquid epoxy adhesive compound mixed with spacers. The diameter of the spacers was 8 millimeters. Liquid crystal was injected into the space between the glass plates through the capillary phenomenon at room temperature. The liquid crystal had the transition temperature of 62 degrees in centigrade, and the refractive index was 1.586/1.510 to 633 nanometer-wavelength light. The injection port was sealed with the epoxy adhesive compound. Thus, a liquid crystal display element was obtained. The liquid crystal displaying element was subjected to the isotropic treatment in an oven at 90 degrees in centigrade for 2 hours. The orientation of the liquid crystal was uniformed.

Figure 7:
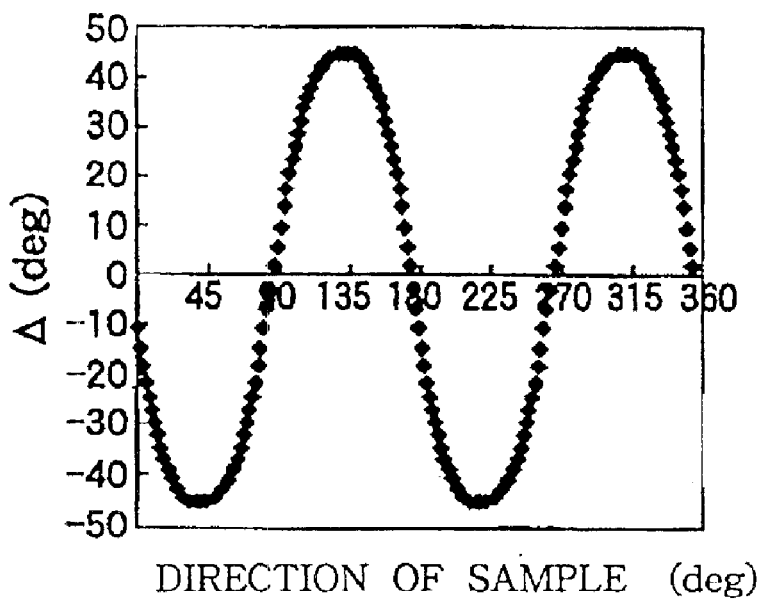
FIG. 7 is a graph showing dependence of a phase difference on the direction of another sample.
Figure 8:
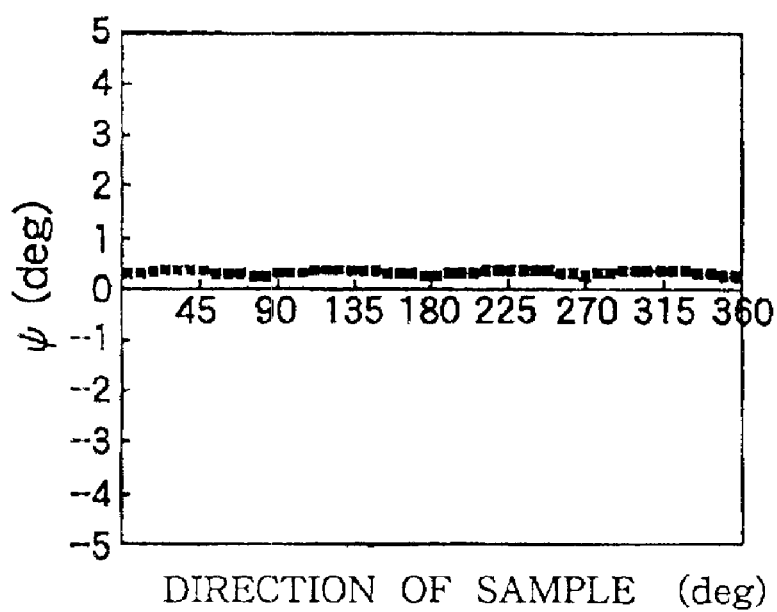
FIG. 8 is a graph showing dependence of an amplitude radio on the direction of the sample.

The direction dependency of the polarization was measured for transmitted light passing through sample B. FIGS. 7 and 8 show the directional dependency of the phase difference $\Delta$ and the directional dependency of the amplitude ration $\psi$. The directional dependency of the polarization was so weak that the twist angle and the cell gap were hardly determined through the prior art method. However, the cell gap and the twist angle were determined through the method according to the present invention. The method was similar to that of the first embodiment. In the method according to the present invention, the cell gap range and the twist angle range was from 4 microns to 10 microns and from 20 degrees to 90 degrees. The cell gap and the twist angle were evaluated to be 8.08 microns and 44.8 degrees.

Third Embodiment

Figure 9:
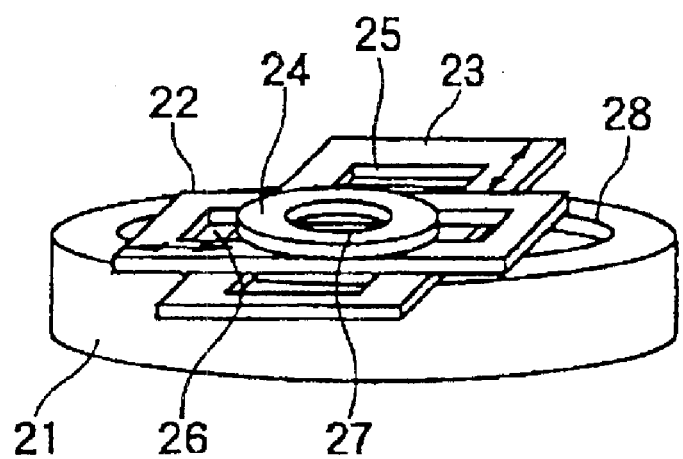
FIG. 9 is a perspective view showing a sample stage incorporated in another evaluating system.

An evaluating system implementing the third embodiment is similar to that shown in FIG. 1 except for the sample stage. The sample stage 104 of the evaluating system implementing the first embodiment is replaced with a sample stage movable on a virtual plane parallel to the major surface of the sample 103 as shown in FIG. 9. In detail, the sample stage includes a rotational stage 21, two movable stages 22/23 mounted on the rotational stage 21 and a retaining stage 24 attached to the movable stage 22. The rotational stage 21 has a ring shape, and is rotatable around a center axis vertically passing through the inner space 28 thereof. The center axis is coincident with the optical axis. The movable stage 23 has a frame configuration, and is mounted on the rotational stage 21. The movable stage 23 allows the optical axis to pass through the inner space 25 thereof. The stage 23 is uni-directionally reciprocally movable on the rotational stage 21 as indicated by an arrow drawn thereon. The other movable stage 22 also has a frame configuration, and is mounted on the movable stage 23. The movable stage 22 allows the optical axis to pass through the inner space 26 thereof. The stage 22 is also uni-directionally reciprocally movable on the movable stage 23 as indicated by an arrow drawn thereon. The moving direction of the stage 22 is perpendicular to the moving direction of the stage 23. The retaining stage 24 is attached to the movable stage 22, and has a ring shape. The optical axis passes through the inner space 27 of the retaining stage 24.

The cell gap and the twist angle were measured for sample A. Sample A was attached to the retaining stage 24. The movable stages 22/23 appropriately moved sample A so as to make a part of sample A aligned with the optical axis. The light beam was radiated from the light source 101 to sample A, and transmitted light was fallen onto the photo-detector 106. The rotational stage 21 was driven for rotation, and the direction dependency of the polarization of the transmitted light was measured. The movable stages 22/23 moved sample A so as to make another part aligned with the optical axis, and the directional dependency was measured.

Figure 10:
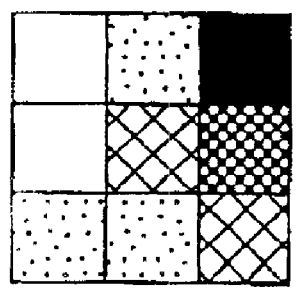
FIG. 10 is a view showing a dispersion of cell gap on a sample.
Figure 10:
Figure 10:
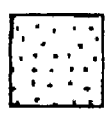
Figure 10:
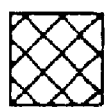
Figure 10:
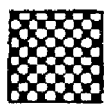
Figure 10:
Figure 11:
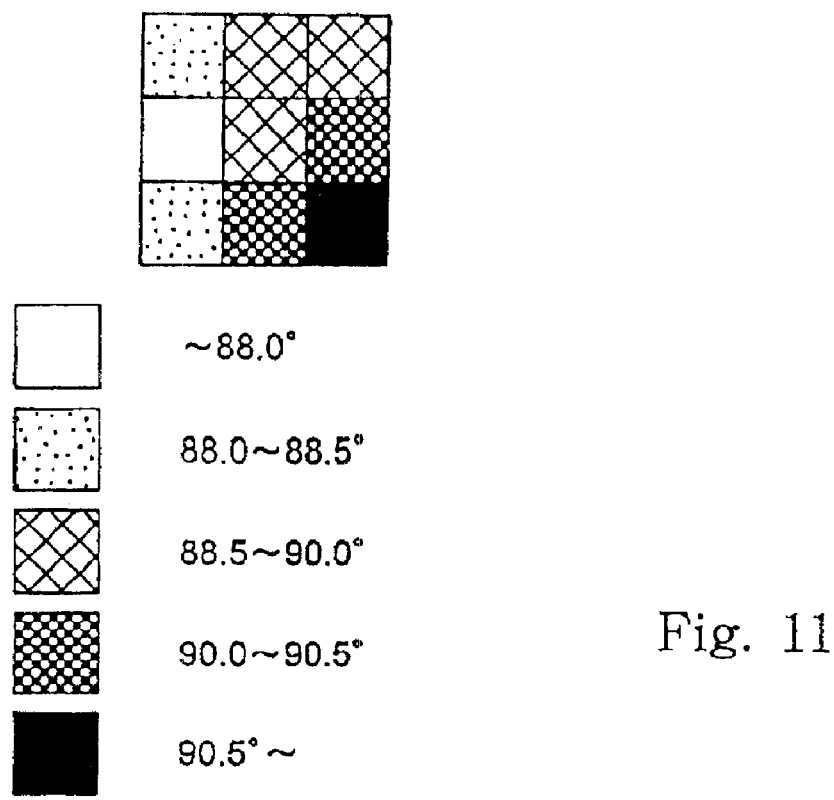
FIG. 11 is a view showing a dispersion of twist angle on the sample.

After the measurement, the cell gap and the twist angle were determined for each part of sample A in the similar manner to sample A in the first embodiment. Since the mean tilt angle of sample A was small, even when the mean tilt angle was adjusted to zero, the variation of calculated twist angle and the variation of calculated cell gap were little. For this reason, the mean tilt angle of the liquid crystal was adjusted to zero in all the parts of sample A, and the cell gap and the twist angle were determined. The measurement was repeated at intervals of 2 millimeters so that sample A was virtually divided into nine parts like a lattice. The cell gap and the twist angle were dispersed as shown in FIGS. 10 and 11.

Fourth Embodiment

Figure 12:
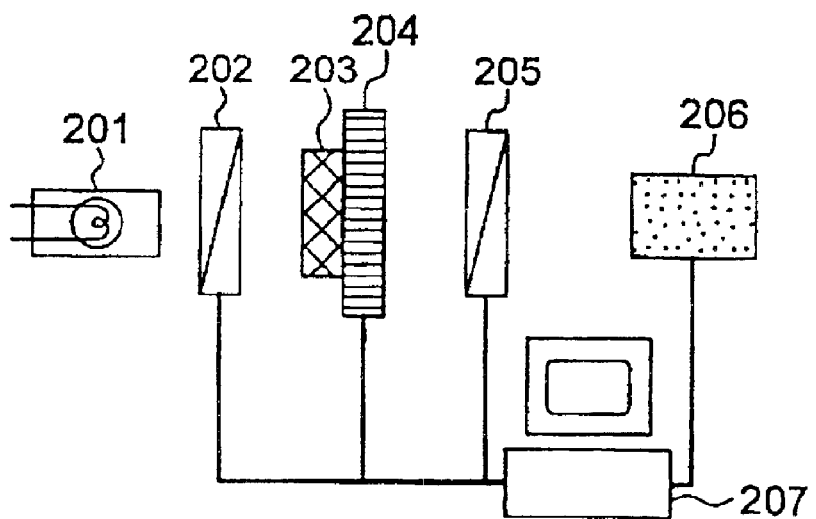
FIG. 12 is a schematic view showing yet another evaluating system according to the present invention.

FIG. 12 shows yet another evaluating system embodying the present invention. As described hereinbefore, the sample stage moves and rotates a sample on a virtual plane to which the optical axis is normal in the evaluating system implementing the third embodiment. The sample is rotated for varying the direction of sample in the second embodiment. In the evaluating system implementing the fourth embodiment, a sample is not rotated, but a polarizer is driven for rotation. The evaluating system implementing the fourth embodiment comprises a light source 201, a polarizer 202, a movable stage 204 for retaining a sample 203, an analyzer 205, a photo-multiplier 206 and a computer system 207.

The light source 201 is implemented by a sodium lamp, and radiate a light beam through the polarizer 202 to the sample 203. Transmitted light passes through the analyzer 205, and is incident onto the photo-multiplier 206. The polarizer 202 is attached to a rotational stage equipped with an encoder, and is driven for rotation around the optical axis. The movable stage 204 two-dimensionally moves the sample 203 on a virtual plate to which the optical axis is normal. The analyzer 205 is also attached to a rotational stage equipped with an encoder, and is driven for rotation around the optical axis.

The computer system 207 is connected to the rotational stage for the polarizer 202, the two-dimensionally movable sample stage 204, the rotational stage for the analyzer 205 and the photo-multiplier 206. The computer system 207 controls the directions of the polarizer/analyzer 202/205 and the position of the sample stage 204, and fetches pieces of data information representative of the light intensity. The computer system 207 calculates the direction dependency of the polarization of the transmitted light, and determines the cell gap of the sample 203, the twist angle of the sample 203 and the mean tilt angle of liquid crystal.

Figure 13:
FIG. 13 is a view showing a dispersion of cell gap on a sample.
Figure 14:
FIG. 14 is a view showing a dispersion of twist angle on the sample.

Sample A was mounted on the sample stage 204, and the sample stage 204 was linearly moved at intervals of 4 millimeters for determining a dispersion of twist angle and a dispersion of cell gap. The mean tilt angle was assumed to be zero. The dispersion of twist angle and the dispersion of cell gap were shown in FIGS. 13 and 14, respectively.

Figure 15:
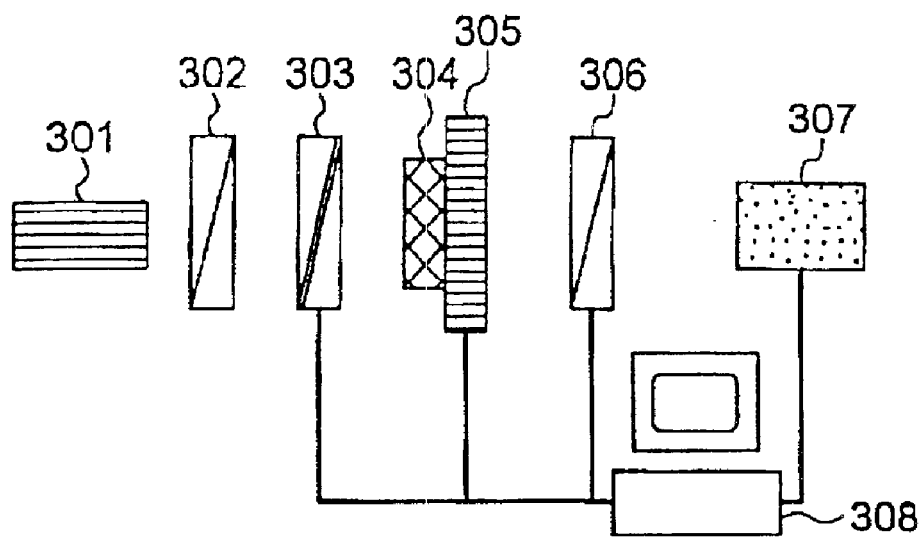
FIG. 15 is a schematic view showing a modification of the evaluating system shown in FIG. 12.

A phase plate 303 such as, for example, a phase plate 303 such as, for example, a half wavelength plate may be inserted between a polarizer 302 and a sample 304 as shown in FIG. 15. In this instance, the direction of sample is fixed, and the phase plate 303 varies the direction of polarization. The polarizer 302 is stationary, and the phase plate 303 is driven for rotation under the control of a computer system 308. A light source, a two-dimensionally movable stage, an analyzer and a photo-multiplier are labeled with references 301, 305, 306 and 307, respectively. The sample stage 305 may be stationary.

Fifth Embodiment

In the second embodiment, when the twist angle range and the cell gap range are from 20 degrees to 60 degrees and from 9 microns to 20 microns, respectively, the sum of squares at the twist angle of 44.7 degrees and the cell gap of 16.35 microns is equal to the sum of square at the twist angle 44.8 degrees and the cell gap of 8.08 microns. This means that the twist angle and the cell gap are not uniquely determined for a sample the cell gap of which is unknown.

Figure 16:
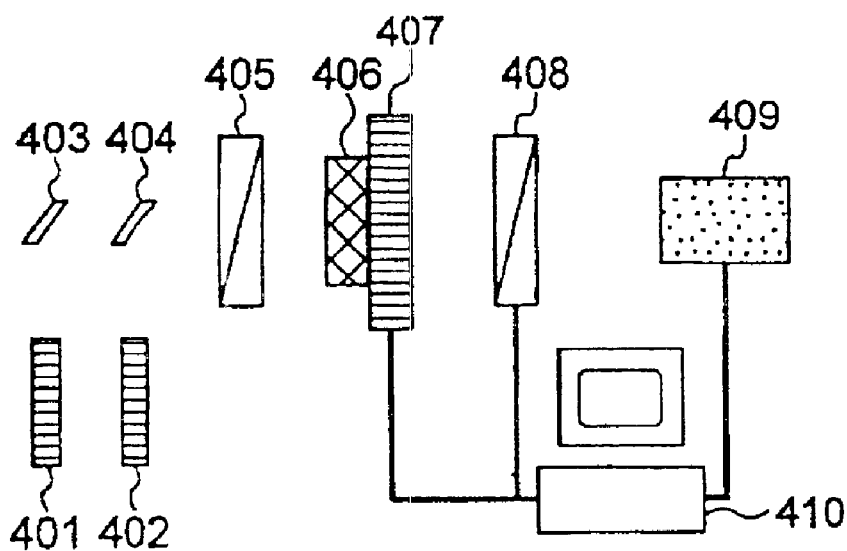
FIG. 16 is a schematic view showing yet another evaluating system according to the present invention.

In order to uniquely determine the cell gap of a sample and the twist angle of the sample and the mean tilt angle of liquid crystal, two light sources 401 and 402 are incorporated in an evaluating system implementing the fifth embodiment as shown in FIG. 16.

In detail, the evaluating system comprises the two light sources 401/402, a reflection mirror 403, a half-mirror 404, a polarizer 405, a rotational sample stage 407 for retaining a sample 406, an analyzer 408, a photo-detector 409 implemented by a photo-multiplier and a computer system 410. The light source 401 is a He-Ne laser emitting device, and the other light source 402 is a light emitting diode. The light emitting diode 402 generates 688 nanometer-wavelength light, and is different in wavelength from the light beam radiated from the other light source 401. The light source 401 radiates the light beam to the reflection mirror 403, and the reflection mirror 403 directs the light beam toward the sample 406. The light beam passes through the half mirror 404 and the polarizer 405, and is incident onto the sample 406. On the other hand, the other light beam is radiated from the light source 402, and is reflected on the half mirror 404 toward the sample 406. The rotational stage 407 is equipped with an encoder, and drives the sample 406 for rotation around the optical axis. The analyzer 408 is also rotational around the optical axis, and is equipped with an encoder. The rotational stage 407 and the analyzer 408 are controlled by the computer system 410. The photo-detector 409 is implemented by a photo-multiplier, and determines the intensity of transmitted light.

The photo-detector 409 supplies pieces of data information representative of the intensity of the transmitted light to the computer system 410. The computer system 410 calculates the directional dependency of the polarization of the transmitted light on the basis of the pieces of data information representative of the intensity of the transmitted light, and determines the cell gap of the sample 406, the twist angle of the sample 406 and the mean tilt angle of liquid crystal confined in the sample 406. In the measurement, the two orthogonal axes are assumed on a virtual plane perpendicular to the optical axis, and the electric field vector of the light is decomposed into an s-component parallel to one of the orthogonal axes and a o-component parallel to the other of the orthogonal axes. The polarization is measured for each of the light beams radiated from the light sources 401/402. While one of the light sources 401/402 is radiating the light beam, the other light source 402/401 is turned off. Otherwise, both light sources 401/402 are energized, and a shield plate selectively interrupts the light beams.

The polarizer 405 was adjusted to 45 degrees with respect to the two orthogonal axes so that the ratio between the s-component of the incident light and the p-component of the incident light was fallen to 1:1. Thus, the linearly polarized light was incident onto the sample 406. The analyzer 408 was driven for rotation, and the polarization of the transmitted light was determined on the basis of the dependence of the light intensity on the direction of the analyzer 408. The light intensity was measured at intervals of 2 degrees. In other words, the analyzer 408 was sequentially changed to 180 directions, and the light intensity was measured for the light beams.

The measuring results for the 688 nanometer-wavelength light was analyzed in the cell gap range from 4 microns to 10 microns and the twist angle range from 20 degrees to 70 degrees, and the twist angle and the cell gap were estimated to be 45.0 degrees and 8.09 microns. If the twist angle range and the cell gap were changed to 20 degrees to 60 degrees and from 9 microns to 20 microns, the twist angle and the cell gap were estimated to be 105.2 degrees and 15.57 microns, which were widely different from those estimated by using the He-Ne laser emitting device. For this reason, the cell gap and the twist angle were determined to be 44.8 degrees to 45.0 degrees and 8.08 microns to 8.09 microns for sample B.

Figure 17:
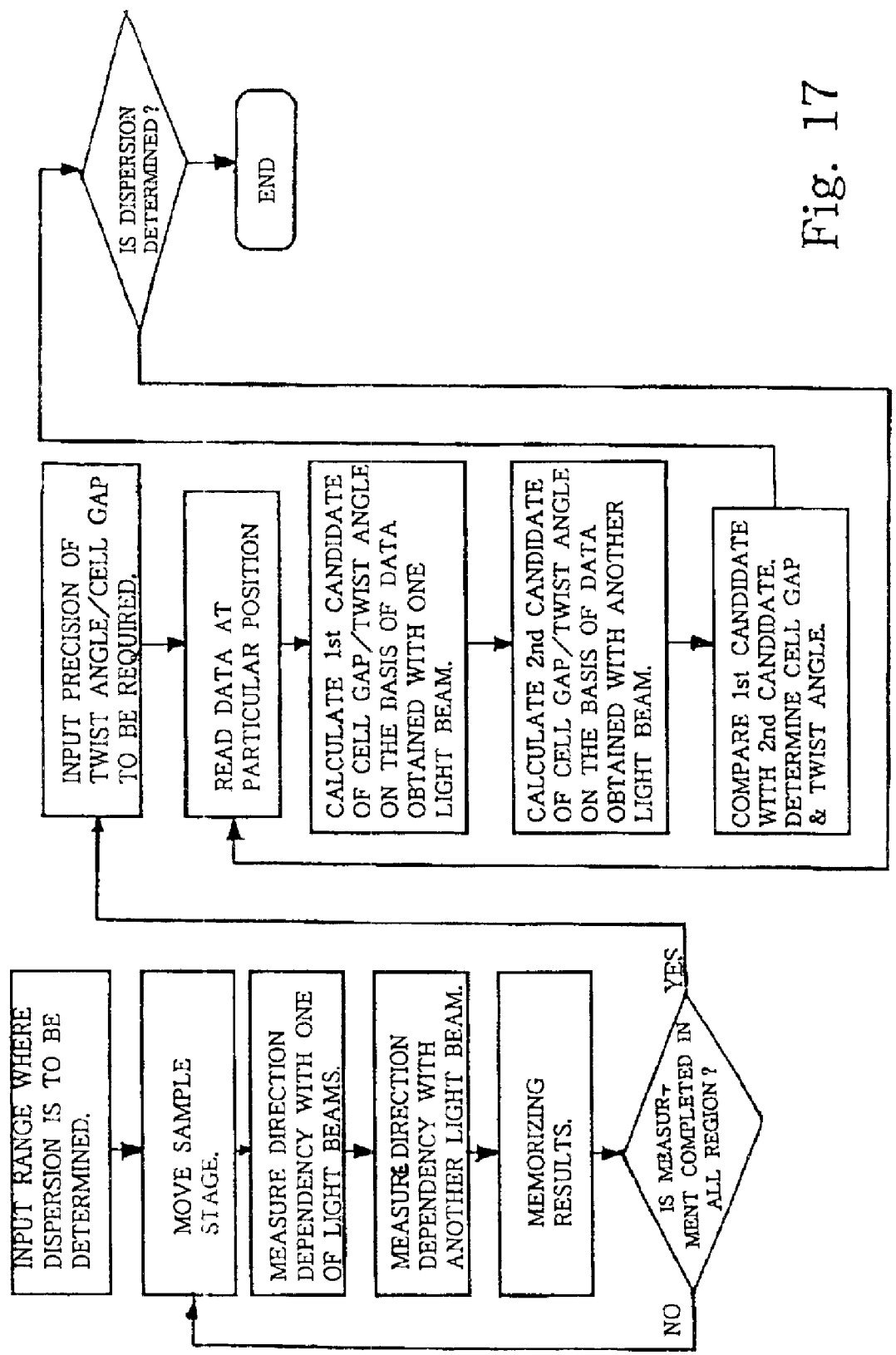
FIG. 17 is a flowchart showing a computer program for the evaluating system.

The evaluating system shown in FIG. 17 may be remodeled like those shown in FIGS. 9 and 12 for determining a dispersion of the polarization. FIG. 17 shows a computer program sequence for the method implementing the fifth embodiment.

Sixth Embodiment

Figure 18:
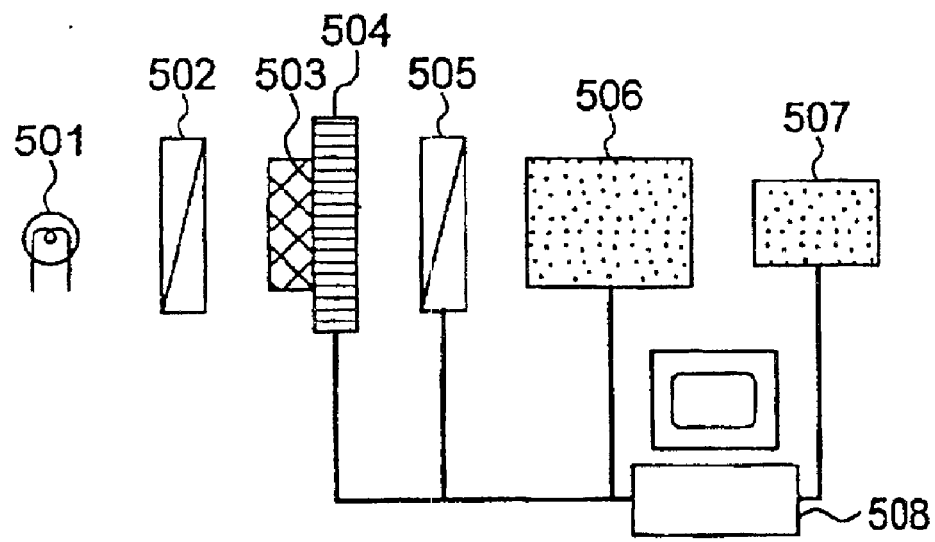
FIG. 18 is a schematic view showing still another evaluating system according to the present invention.

FIG. 18 shows still another evaluating system embodying the present invention. The evaluating system comprises a light source 501, a polarizer 502, a rotational stage for retaining a sample 503, an analyzer 505, a spectroscope 506, a photo-multiplier 507 and a computer system 508. The light source 501 is implemented by a halogen lamp. The sample stage 504 is rotatable around the optical axis, and is equipped with an encoder. The analyzer 505 is also rotatable around the optical axis, and is equipped with an encoder. The light source 501 radiates a light beam, and the light beam passes through the polarizer 502. The polarized light is incident onto the sample 503, and the spectroscope 506 disperses transmitted light for producing monochromatic light components. The monochromatic light components are incident onto the photo-multiplier 507. The computer system 508 controls the direction of the sample stage 504, the direction of the analyzer 507 and the spectroscope 506. The computer system 508 is further connected to the photo-multiplier 507, and fetches pieces of data information representative of the light intensity. The computer system 508 calculates the directional dependency of the polarization on the basis of the light intensity, and determines the cell gap of the sample 503, the twist angle of the sample 503 and the means tilt angle of liquid crystal confined in the sample 503.

The electric field vector of the light is decomposed into an s-component and a p-component, and the s-component and the p-component are in parallel to orthogonal axes of a rectangular coordinate system. The polarizer 502 is oriented at 45 degrees with respect to each of the orthogonal axes, and linearly polarizes the incident light which has the s-component and the p-component at 1:1. The analyzer 505 is rotated at intervals of 2 degrees, and the measurement is carried out for each of the 180 directions. The spectroscope 506 disperses the transmitted light into monochromatic light components different in wavelength from one another. Though not shown in FIG. 18, the monochromatic light components are selectively fallen into the photo-multiplier 507. Namely, the computer system selects one of the monochromatic light components, and instructs the spectroscope 506 to pass the selected monochromatic light component. The selected monochromatic light component is incident onto the photo-multiplier 507. However, the other monochromatic light components are internally shielded.

Although the direction dependency of the polarized light is determined for determining the cell gap of the sample 503, the twist angle of the sample 503 and the mean tilt angle of the liquid crystal as similar to the method implementing the fifth embodiment, the cell gap is determined on the basis of wavelength dependency of the polarization of the transmitted light. The sample 503 keeps the position unchanged. A monochromatic light component is selected, and the spectroscopy 506 is regulated in such a manner as to pass the selected monochromatic light component. The intensity of the selected monochromatic light component is measured by the photo-multiplier 507, and determines angle dependence of the polarization of the selected monochromatic light component. There are plural candidates of the combination of the twist angle of the sample 503, the cell gap of the sample 503 and the means tilt angle of the liquid crystal. The plural candidates are to satisfy the angle dependency. The wavelength dependency of the polarization of the transmitted light is calculated on the basis of each of the candidates.

Subsequently, the wavelength dependency of the polarization of the transmitted light under the condition that the sample 503 keeps the position unchanged. The wavelength dependency determined through the measurement is compared with the wavelength dependency determined through the calculation. When the wavelength dependency calculated for one of the candidates is matched with the wavelength dependency determined through the measurement, the cell gap, the twist angle and the means tilt angle are estimated to be identical with those of the candidate.

Figure 19:
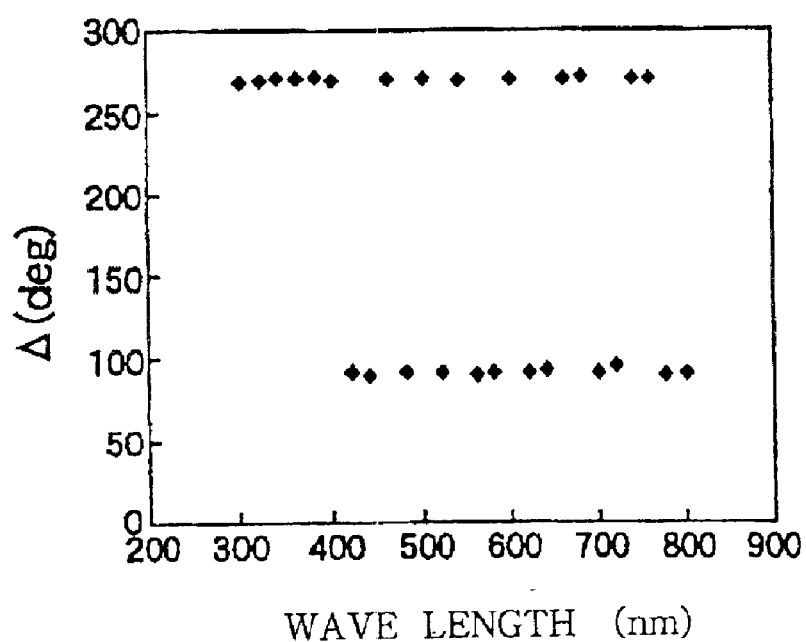
FIG. 19 is a graph showing relation between the phase difference and the wavelength of transmitted light determined through a measurement.
Figure 20:
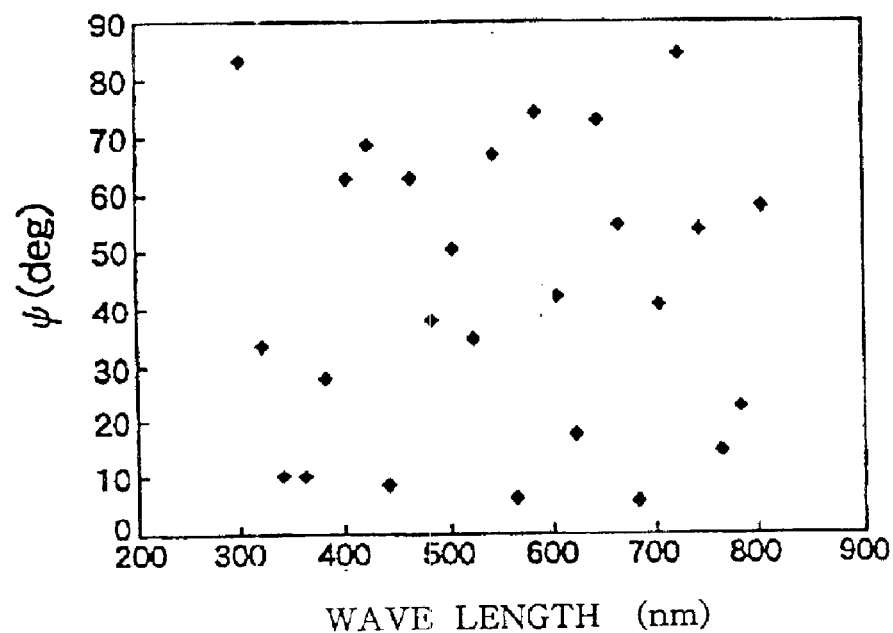
FIG. 20 is a graph showing relation between the amplitude ratio and the wavelength of the transmitted light determined through a measurement.

FIGS. 19 and 20 show the wavelength dependency of the polarization of the transmitted light passing through sample B. FIG. 19 teaches the relation between the phase difference Δ and the wavelength, and FIG. 20 teaches the relation between the amplitude ratio ψ and the wavelength. The wavelength of the transmitted light was varied at intervals of 20 nanometers, and the wavelength dependency shown in FIGS. 19 and 20 was determined on the basis of the measured light intensity.

Figure 21:
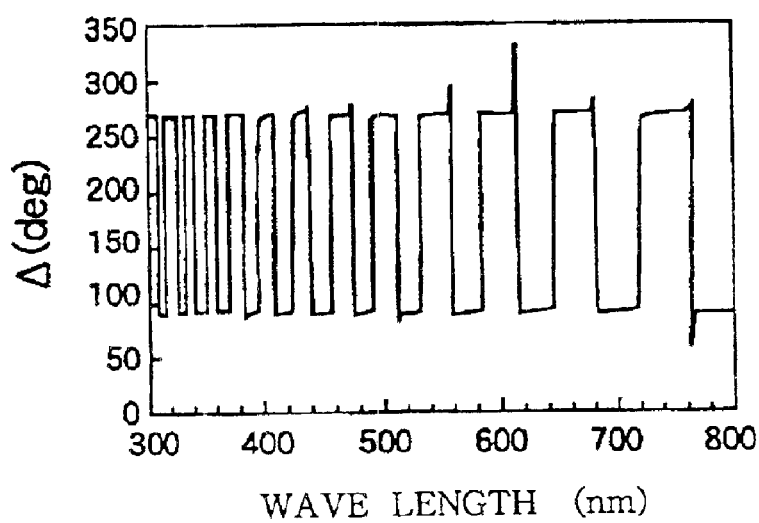
FIG. 21 is a graph showing relation between the phase difference and the wavelength determined through a calculation.
Figure 22:
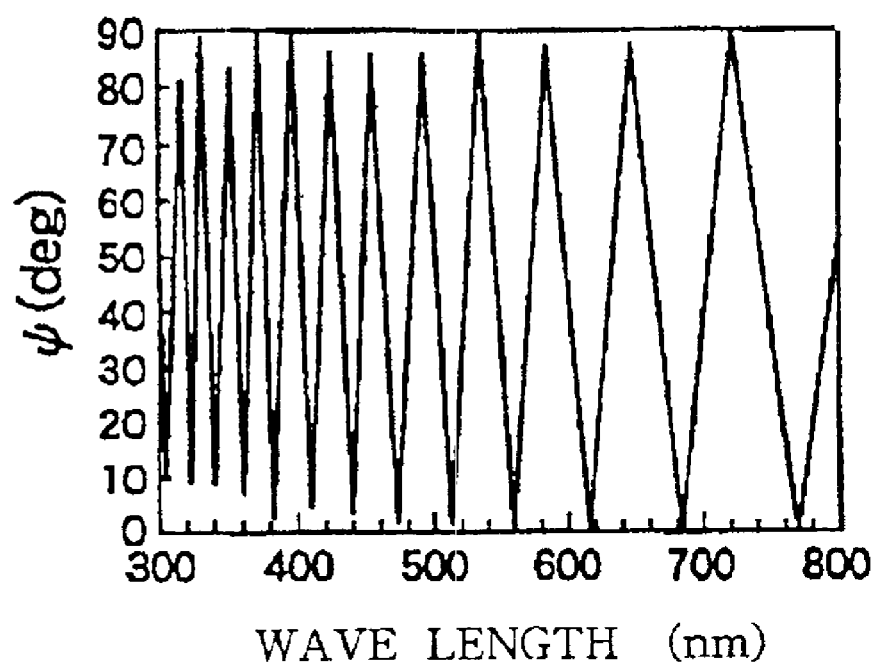
FIG. 22 is a graph showing relation between the amplitude ratio and the wavelength determined through the calculation.

FIGS. 21 and 22 show the wavelength dependency calculated for two combinations of the twist angle and the cell gap. The first combination was the twist angle of 44.7 degrees and the cell gap of 16.35 microns, and the second combination was the twist angle of 44.8 degrees and the cell gap of 8.08 microns. The sample B was adjusted to zero degree.

Figure 23:
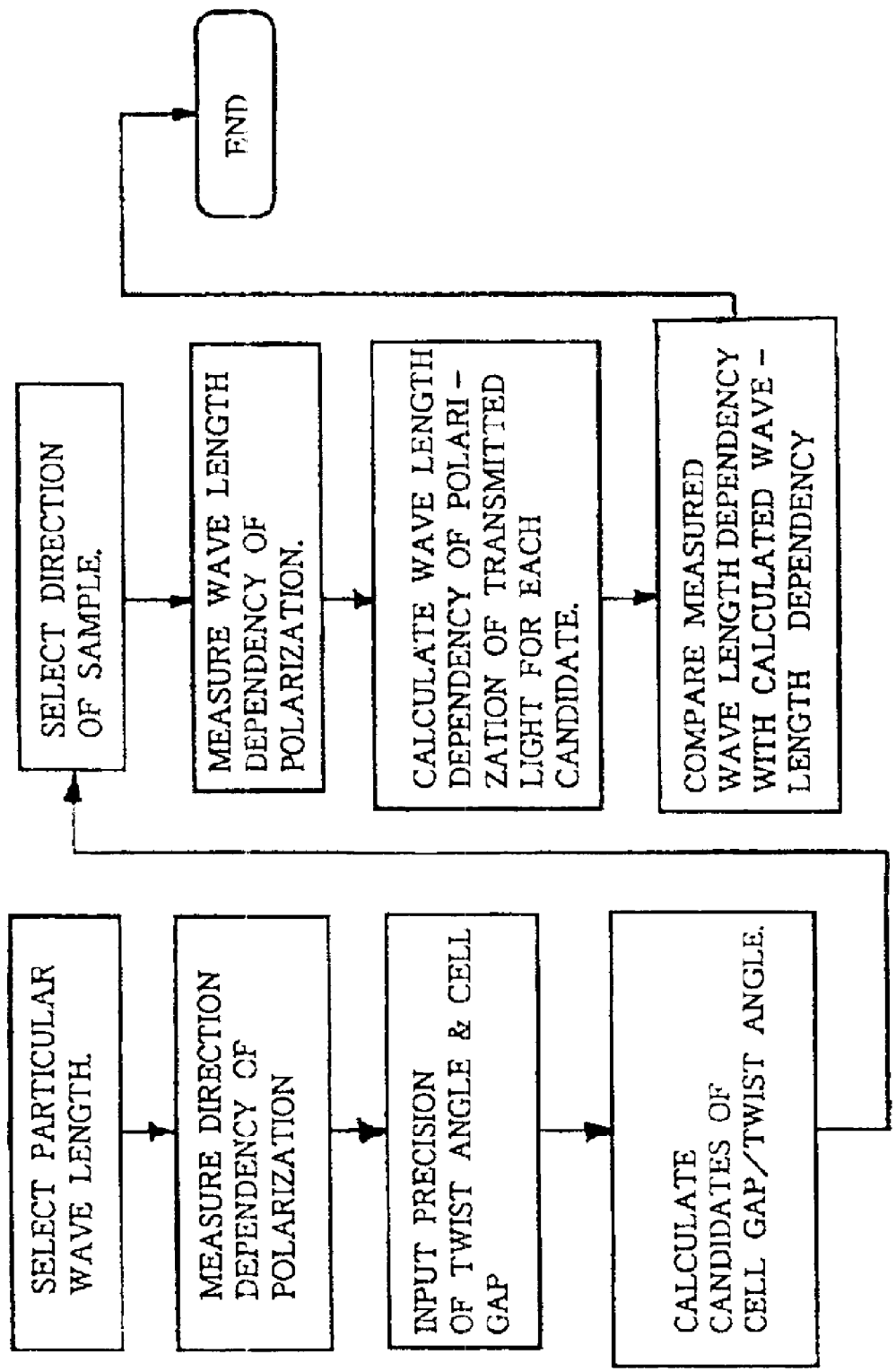
FIG. 23 is a flowchart showing a computer program for another method.

Comparing the wavelength dependency determined through the measurement with the wavelength dependency determined through the calculation, it is understood that the wavelength dependency for the second combination is analogous to the wavelength dependency determined through the measurement. For this reason, the twist angle and the cell gap of sample B were estimated to be 44.8 degrees and 8.08 microns. The method described hereinbefore is realized by a computer program shown in FIG. 23.

The evaluating system shown in FIG. 18 may be remodeled like those implementing the third and fourth embodiments.

Seventh Embodiment

Although the method implementing the sixth embodiment determines the wavelength dispersion, the wavelength dependency of the transmitted light intensity is determined under the condition that a sample and an analyzer keep the directions unchanged.

Figure 24:
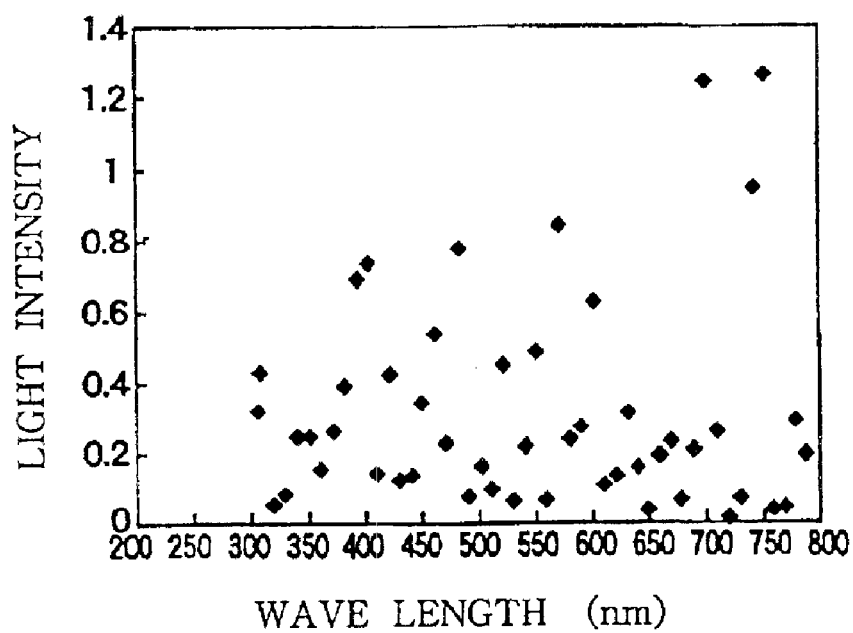
FIGS. 24-26 are graphs showing relationships between wavelength and light intensity.
Figure 25:
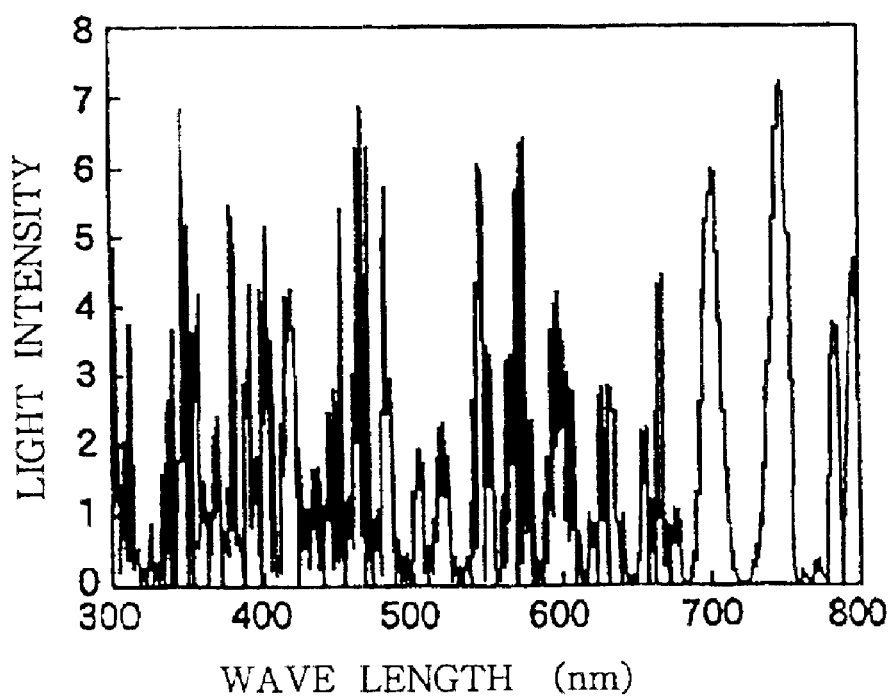
Figure 26:
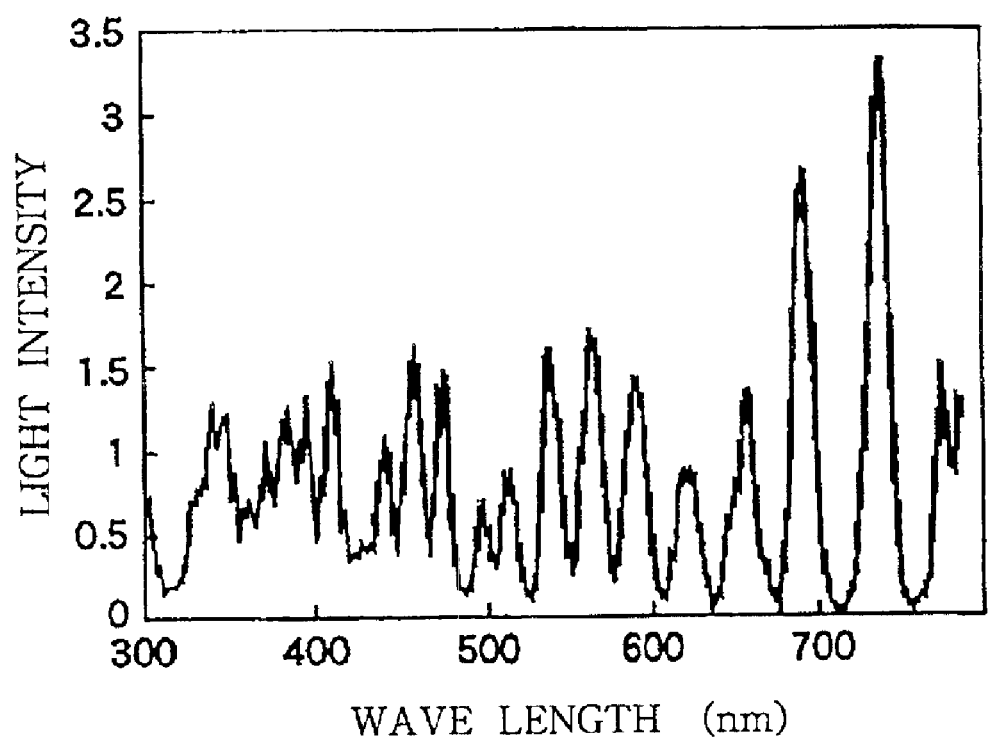

Sample B was adjusted to zero degree, and the analyzer was adjusted to 90 degrees. The light source radiated the light beam through the polarizer to sample B, and the transmitted light was incident through the analyzer onto the photo-detector. The wavelength dependency of the transmitted light intensity was plotted as shown in FIG. 24. The wavelength dependency of the transmitted light intensity was calculated for the first combination of the cell gap and the twist angle and the second combination of the cell gap and the twist angle. The twist angle and the cell gap of the first combination were 44.8 degrees and 8.08 microns, and the twist angle and the cell gap of the second combination were 44.7 degrees and 16.35 microns. Since the resolution of the spectroscopy of 10 was not taken into account, the plots in FIG. 25 were not consistent with the plots in FIG. 24. The resolution of the spectroscopy was 10 nanometers. When the resolution was taken into account, the calculation resulted in plots shown in FIG. 26, and the plots were analogous to the plots representative of the measured wavelength dependency. From the experiment, the twist angle and the cell gap were matched with 44.8 degrees and 8.08 microns of the sixth embodiment. The method described hereinbefore is expressed by a computer program.

Eighth Embodiment

Although the twist angle of sample B was adjusted to 50 degrees, the twist angel and the cell gap are estimated to be 44.8 degrees and 8.08 microns through the methods implementing the second, fifth, sixth and seventh embodiments. The regulatory ability A for the orientation of liquid crystal is expressed as $$A=2K22\phi t/(d\times\sin(2\phi 0-2\phi t))$$

where $\phi 0$ is the twist angle of the sample, $\phi t$ is the twist angle measured in the liquid crystal and K22 is the twist elastic coefficient. The twist elastic coefficient K22 of sample B is 9.3 pN. Then, the regulatory ability A is $9.97\times 10^{-6}$ J/m².

As will be appreciated from the foregoing description, the monochromatic light source, the polarizer, the analyzer and the photo-detector are combined according to the present invention. The phase plate is further combined, if necessary. The predetermined polarized light is incident into the sample or a liquid crystal display element, and the direction dependency of the polarization of the transmitted light is measured. The cell gap and the twist angle are accurately determined on the basis of the results. When the direction dependency is accurately determined, the mean tilt angle of liquid crystal is further determined.

Even if the sample is fixed to a certain direction, it is possible to measure the dependence of the polarization of the transmitted light on the polarization of the incident light measured by varying the polarization of the incident light. The twist angle of the liquid crystal display element, the cell gap thereof and the mean tilt angle of the liquid crystal are determined on the basis of the dependency.

Plural light components are available for the measurement. The plural light components are different in wavelength from one another. The direction dependency of the polarization of the transmitted light or the dependence of the polarization of the transmitted light on the polarization of the polarization of the incident light is measured for each of the plural light components. Using the measurement, the twist angle of the liquid crystal display element, the cell gap thereof and the mean tilt angle of the liquid crystal are uniquely determined.

White light is also available for the measurement. The white light is incident onto a sample, and a particular wavelength light component is extracted from the transmitted light. Using the particular wavelength light component, the direction dependency of the polarization of the particular wavelength light component is determined. Otherwise, the sample is fixed to a predetermined direction, and the polarization is varied for determining the dependence of the polarization of the transmitted light component on the polarization of the incident light component. The wavelength dependency of the transmitted light intensity may be determined under the conditions that the incident light is fixed to a predetermined polarization or the sample/analyzer are respectively fixed to certain directions. The twist angle of the liquid crystal display element are the cell gap thereof are uniquely determined. When the accuracy is high, the mean tilt angle is also determined.

The movable stages are available for determining a dispersion of polarization on the sample. The movable stages may move a sample uni-directionally or two-dimensionally. The movable stages allow an analyst to virtually divide a sample into plural portions, and the evaluating system repeats the estimation for the plural portions. This results in a dispersion of polarization on the sample.

When the twist angle and the cell gap are determined, the regulatory ability for orientation of a liquid crystal display element is calculated on the basis of the twist angle, the cell gap and the twist elastic coefficient of the liquid crystal.

Although particular embodiments of the present invention have been shown and described, it will be apparent to those skilled in the art that various changes and modifications may be made without departing from the spirit and scope of the present invention.

What is claimed is:

1. A method for evaluating a liquid crystal display element, comprising the steps of:
    a) radiating a light beam having a certain waveband and a predetermined polarization to said liquid crystal display element so as to produce a transmitted light beam;
    b) measuring at least one of a directional dependency of a polarization of said transmitted light beam and a wavelength dependency of said polarization of said transmitted light beam; and
    c) determining at least one of a dispersion of a twist angle, of the liquid crystal confined in said liquid crystal display element, a mean tilt angle of said liquid crystal and a thickness of said liquid crystal on the basis of said at least one of said directional dependency and said wavelength dependency.

2. A method for evaluating a liquid crystal display element, comprising the steps of:
    a) radiating a light beam having a certain waveband and a predetermined polarization to a portion of said liquid crystal display element so as to produce a transmitted light beam;
    b) measuring at least one of a directional dependency of a polarization of said transmitted light beam and a wavelength dependency of said polarization of said transmitted light beam;
    c) moving said liquid crystal display element on a virtual plane perpendicular to the optical axis of said light beam so that said light beam is incident onto another portion of said liquid crystal display element;
    d) repeating said step b) for said another portion of said liquid crystal display element; and
    e) determining a dispersion of at least one of a twist angle, of the liquid crystal confined in said liquid crystal display element, a mean tilt angle of said liquid crystal and a thickness of said liquid crystal on the basis of said at least one of said directional dependency and said wavelength dependency.

3. An information storage medium for storing a computer program representative of a method for evaluating a liquid crystal display element, said method comprising the steps of:
    a) radiating a light beam having a certain waveband and a predetermined polarization to said liquid crystal display element so as to produce a transmitted light beam;
    b) measuring at least one of a directional dependency of a polarization of said transmitted light beam and a wavelength dependency of said polarization of said transmitted light beam; and c) determining at least one of a dispersion of a twist angle, of the liquid crystal confined in said liquid crystal display element, a mean tilt angle of said liquid crystal and a thickness of said liquid crystal on the basis of said at least one of said directional dependency and said wavelength dependency.

4. An information storage medium for storing a computer program representative of a method for evaluating a liquid crystal display element, said method comprising the steps of:

a) radiating a light beam having a certain waveband and a predetermined polarization to a portion of said liquid crystal display element so as to produce a transmitted light beam;

b) measuring at least one of a directional dependency of a polarization of said transmitted light beam and a wavelength dependency of said polarization of said transmitted light beam;

c) moving said liquid crystal display element on a virtual plane perpendicular to the optical axis of said light beam so that said light beam is incident onto another portion of said liquid crystal display element;

d) repeating said step b) for said another portion of said liquid crystal display element; and e) determining a dispersion of at least one of a twist angle, of the liquid crystal confined in said liquid crystal display element, a mean tilt angle of said liquid crystal and a thickness of said liquid crystal on the basis of said at least one of said directional dependency and said wavelength dependency.

5. An evaluating apparatus for a liquid crystal display element, comprising:

a light source radiating a light beam toward said liquid crystal display element;

a polarizer provided between said light source and said liquid crystal display element for producing a polarized light beam from said light beam;

a sample stage keeping said liquid crystal display element on an optical axis of said polarized light beam;

an analyzer provided on said optical axis of said polarized light beam;

a light intensity measuring unit for measuring a light intensity of a transmitted light beam passing through said analyzer and producing data information representative of said light intensity; and a data processing system connected to said light source, said polarizer, said sample stage and said analyzer for controlling the attitude thereof and to said light intensity measuring unit for receiving said data information, and measuring at least one of a directional dependency of a polarization of said transmitted light beam and a wavelength dependency of said polarization of said transmitted light beam so as to determine at least one of a twist angle of the liquid crystal confined in said liquid crystal display element, a mean tilt angle of said liquid crystal and a thickness of said liquid crystal.

6. The evaluating apparatus as set forth in claim 5, in which said sample stage and said analyzer includes encoders, respectively, and are driven for rotation around said optical axis under the control of said data processing system so that said data processing system determines said at least one of said twist angle, said mean tilt angle and said thickness on the basis of said directional dependency.

7. The evaluating apparatus as set forth in claim 5, in which said sample stage includes a first stage rotational around said optical axis, a second stage mounted on said first stage and reciprocally movable in a first direction on a virtual plane perpendicular to said optical axis and a third stage mounted on said second stage, retaining said liquid crystal display element and movable in a second direction perpendicular to said first direction on said virtual plane.

8. The evaluating apparatus as set forth in claim 7, in which said data processing system controls an angular direction of said first stage around said optical axis, a position of said second stage in said first direction, a position of said third stage in said second direction and an angular position of said analyzer around said optical axis so that said data processing system determines a dispersion of said at least one of said twist angle, said mean tilt angle and said thickness on the basis of said directional dependency.

9. The evaluating apparatus as set forth in claim 5, in which said data processing system controls an angular position of said polarizer around said optical axis and an angular position of said analyzer around said optical axis so that said data processing system determines at least one of said twist angle, said mean tilt angle and said thickness on the basis of said directional dependency.

10. The evaluating apparatus as set forth in claim 9, in which said sample stage includes a first stage reciprocally movable in a first direction on a virtual plane perpendicular to said optical axis and a second stage reciprocally movable in a second direction perpendicular to said first direction on said virtual plane so that said data processing system determines a dispersion of said at least one of said twist angle, said mean tilt angle and said thickness.

11. The evaluating apparatus as set forth in claim 5, further comprising a phase plate provided between said polarizer and said liquid crystal display element; and said data processing system controls an angular position of said phase plate around said optical axis and an angular position of said analyzer around said optical axis so that said data processing system determines at least one of said twist angle, said mean tilt angle and said thickness on the basis of said directional dependency.

12. The evaluating apparatus set forth in claim 11, in which said sample stage includes a first stage reciprocally movable in a first direction on a virtual plane perpendicular to said optical axis and a second stage reciprocally movable in a second direction perpendicular to said first direction on said virtual plane so that said data processing system determines a dispersion of said at least one of said twist angle, said mean tilt angle and said thickness.

13. The evaluating apparatus as set forth in claim 5, in which said light source radiates said light beam having plural light components different in wavelength, and said data processing system selects said at least one of said twist angle, said mean tilt angle and said thickness from plural candidates each determined on the basis of said directional dependency.

14. The evaluating apparatus as set forth in claim 13, in which said light source includes plural sources of light respectively radiating said plural light components and plural optical path changing means for directing said plural light components toward said liquid crystal display element through said polarizer.

15. The evaluating apparatus as set forth in claim 14, in which one of said plural optical path changing means is implemented by a reflecting mirror, and another of said plural optical path changing means is implemented by a half mirror positioned between said reflecting mirror and said polarizer.

16. The evaluating apparatus as set forth in claim 5, further comprising a spectroscope provided between said analyzer and said light intensity measuring unit for separating said light beam into plural light components, and said data processing system selects said at least one of said twist angle, said mean tilt angle and said thickness from plural candidates each determined on the basis of said directional dependency.

17. The evaluating apparatus as set forth in claim 5, further comprising a spectroscope provided between said analyzer and said light intensity measuring unit for separating said light beam into plural light components, and said data processing system selects said at least one of said twist angle, said mean tilt angle and said thickness from plural candidates each determined on the basis of said wavelength dependency.

18. The evaluating apparatus as set forth in claim 17, in which said data processing system determines an angle dependency of said polarization of selected one of said light components by changing an angular position of said liquid crystal display element and an angular position of said analyzer, plural combinations of said twist angle, said mean tilt angle and said thickness which satisfy said angle dependency and said wavelength dependency of said polarization by using said component light without changing the angular position of said liquid crystal display element, calculating the wavelength dependency for said combinations, and comparing the calculation results with said wavelength dependency for determining the most appropriate candidate of said twist angle, said mean tilt angle and said thickness.

19. The evaluating apparatus as set forth in claim 17, in which said data processing system determines an angle dependency of said polarization of selected one of said light components by changing an angular position of said liquid crystal display element and an angular position of said analyzer, plural combinations of said twist angle, said mean tilt angle and said thickness which satisfy said angle dependency and said wavelength dependency of a light intensity by using said component light without changing the angular positions of said liquid crystal display element and said analyzer, calculating the wavelength dependency for said combinations, and comparing the calculation results with said wavelength dependency for determining the most appropriate candidate of said twist angle, said mean tilt angle and said thickness.

* * * * *